(12) United States Patent
Grundei et al.

(10) Patent No.: US 6,712,858 B1
(45) Date of Patent: Mar. 30, 2004

(54) REINFORCEMENT ENDOPROSTHESIS

(75) Inventors: Hans Grundei, Lübeck (DE); Rudolf Ascherl, Leipzig (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/856,732

(22) PCT Filed: Nov. 20, 1999

(86) PCT No.: PCT/EP99/00973

§ 371 (c)(1),
(2), (4) Date: Aug. 6, 2001

(87) PCT Pub. No.: WO00/30569

PCT Pub. Date: Jun. 2, 2000

(30) Foreign Application Priority Data

Nov. 26, 1998 (DE) .......................................... 198 54 517
Feb. 3, 1999 (DE) .......................................... 199 04 214

(51) Int. Cl.$^7$ .................................................. A61F 2/30
(52) U.S. Cl. ................................. 623/23.45; 623/23.47
(58) Field of Search .......................... 623/22.42, 23.18, 623/23.45, 23.47, 23.29, 23.3, 23.23, 23.46; 606/62, 63; A61F 2/28, 2/30, 2/32, 2/36, 2/38, 1/00, 1/03

(56) References Cited

U.S. PATENT DOCUMENTS

| | | | |
|---|---|---|---|
| 4,384,373 A | 5/1983 | Sivash | |
| 4,502,160 A * | 3/1985 | Moore et al. ............. | 623/23.47 |
| 4,673,409 A * | 6/1987 | Van Kampen ........... | 623/23.29 |
| 4,892,546 A * | 1/1990 | Kotz et al. ................ | 623/23.45 |
| 5,137,535 A | 8/1992 | Keller | |
| 5,358,524 A | 10/1994 | Richelsoph | |
| 5,433,750 A * | 7/1995 | Gradinger et al. ............. | 623/16 |
| 5,765,957 A * | 6/1998 | Connell ........................ | 403/46 |

FOREIGN PATENT DOCUMENTS

| | | | |
|---|---|---|---|
| DE | 31 38 848 | 4/1983 | |
| DE | 33 36 004 | 6/1985 | |
| DE | 35 35 158 | 4/1987 | |
| DE | 3605630 A1 * | 9/1987 | ............. A61F/2/28 |
| DE | 39 03 438 | 8/1990 | |
| DE | 40 39 064 | 6/1992 | |
| DE | 42 08 247 | 7/1995 | |
| EP | 0 290 767 | 11/1988 | |
| FR | 2 585 945 | 2/1987 | |
| GB | 2 070 939 | 6/1981 | |

* cited by examiner

*Primary Examiner*—David H. Willse
*Assistant Examiner*—Javier G. Blanco
(74) *Attorney, Agent, or Firm*—Cantor Colburn LLP

(57) ABSTRACT

The invention relates to a reinforcement endoprosthesis for use in a femoral bone which is resected at an end of a hip joint and at an end of a knee joint. The endoprosthesis includes a stem part of an artificial hip joint and a condyle part of an artificial knee joint. The connecting part between the stem part and the condyle part is configured as a two-piece intramedullary nail which extends inside the femoral bone. One part of the intramedullary nail is a massive intramedullary nail with a connecting portion for a thread and a thread attached thereto and another part of the intramedullary nail is a hollow intramedullary nail with a female thread matching the thread of the first part. The female thread can be screwed with the thread, thereby allowing a length adjustment of the endoprosthesis.

4 Claims, 1 Drawing Sheet

REINFORCEMENT ENDOPROSTHESIS

TECHNICAL FIELD

This invention concerns a reinforcing endoprosthesis for use in the femoral bone, which is resected both in the area of the ball of the natural hip joint and also in the area of the condyle of the natural knee joint. Accordingly, the reinforcing endoprosthesis has a shaft part in the area of the hip joint and has a condyle part in the area of the knee joint.

BACKGROUND OF THE INVENTION

There are indications in which the stress on the corticalis of the femur must be relieved, since at the time of the indication, clinical pictures like arthritis, rheumatism, arthosis in the knee or osteoporosis in the hip joint area or trauma in the hip or knee joint area make surgical procedures appear necessary, although after therapy, there is hope that the corticalis of the femur can be restored to its natural function after some time.

A tumor endoprosthesis, like the one in DE-A-40 39 064, for example, may not give this only temporary relief of the reinforcing endoprosthesis sought, since the femoral bone must be completely removed to implant this tumor endoprosthesis because of the tumor. This type of endoprosthesis is not suitable for the special clinical picture given above as an example.

U.S. Pat. No. 4,384,373 shows another tumor endoprosthesis. Here, because of the tumor, a correspondingly large bone area is resected which is then no longer capable of a stress-relieving function. Likewise, an attempt is made to leave the patient as much natural bone material as possible. For this reason, the publication proposes using the tumor endoprosthesis in the intramedullar area, whereby the prosthesis has both a condyle part in the area of the knee joint and a bridge simulating the neck of the femur and other areas of the natural femoral bone, on whose end the artificial ball of the hip joint sits. Because of the indication, the residual bone—as already stated—cannot be stressed. The goal of implanting this type of tumor endoprosthesis is to give the patient as much help as possible, so the patient can move forward in the most natural way possible. This type of tumor prosthesis then has a permanent help function.

SUMMARY OF THE INVENTION

This prosthesis is not suitable for the above-mentioned indications.

On this background, the problem of this invention is to provide a reinforcing endoprosthesis for the femoral bone which performs a temporary stress-relieving function and which can be used universally, i.e., can be made of standard components for the individual patient.

This problem is solved by making the connecting part between the shaft part in the hip joint area and the condyle part in the artificial knee joint area with a two-piece intramedullary nail, whereby one part of the intramedullary nail is solid and has a threaded projection with a thread on it, and the other part of the intramedullary nail is hollow and has an inner thread that fits the thread on the first part, which can be screwed onto the thread, whereby the length of the endoprosthesis can be adjusted.

The connecting part works on the principle of a spindle screw. The operator can set the length of the intramedullary nail and hence the connecting part between the parts of the artificial joint for the individual patient and thus prepare the endoprosthesis. The endoprosthesis is composed of standard parts, especially the solid intramedullary nail and the hollow intramedullary nail. The shaft part or condyle part, selected based on the individual patient, can then be coupled to these two parts. The shaft part can preferably be stopped at the solid intramedullary nail by means of a safety screw connected to a conical clamping seat between a conical pin and a conical receptacle. The condyle part is also preferably held on the hollow intramedullary nail by the effect of a conical clamp between a conical receptable and a conical pin, whereby advantageously, a hexagon safety screw is in a corresponding receptacle at the place between the condyle part and the hollow intramedullary nail. This last measure gives it rotational stability.

It is also possible to put the corticalis under compression in relation to the femoral bone by purposely shortening the reinforcing endoprosthesis. This promotes the bone healing process.

When implanting the reinforcing endoprosthesis in the invention, the surgeon proceeds so that first the femur in the hip joint area, unlike the proposal in U.S. Pat. No. 4,384,373 already mentioned, is resected only by removing the neck of the femur with the top of the hip joint and in the knee joint area. Then the solid intramedullary nail, which is connected to a shaft part with a suitable size and shape, etc. for example, is pushed into the medullar space of the femoral bone. From the other side, the second, hollow intramedullary nail is pushed into the medullar space until the thread in the hollow intramedullary nail meets the thread in the solid intramedullary nail. The length of the reinforcing endoprosthesis is set by making a screwing motion with the first intramedullary nail in relation to the second intramedullary nail.

It is an advantage that the dimensions are designed so that the length of the intramedullary nail can vary up to 10 cm. This means that the length can be changed by ±5 cm from its normal position by adjusting the spindle screw.

The stresses that are normally undergone by the natural femur corticalis are now partly cushioned by the reinforcing endoprosthesis. Over time, the stress-relieving function decreases, and the corticalis takes heavier stresses until the natural stress can come back. This period of time for the transition from the stress on the endoprosthesis to the corticalis can be accompanied by prescribing medication for certain clinical pictures, for example, so the corticalis can take stress over time.

One special advantage is the design of the endoprosthesis so that the surface of the shaft part and the structural area of the condyle part on the resected femoral bone, at least partly, have a three-dimensional, open-mesh spatial network structure. The spatial network structure then lies on the spongiosa remaining in the femoral bone and stimulates the growth of bone trabeculae there. After a certain time, the implant is fully organized in the femoral bone and forms a tight bond with it. After the endoprosthesis has completely grown in, the bridging intramedullary nail has practically no stress-relieving function to perform.

When an endoprosthesis is used on a fractured femur, often osteosynthesis plates are used to set the fractured bone parts and mechanically stabilize the fracture site during healing. This works well in practice, but has the disadvantage that the osteosynthesis plates often cannot be set symmetrically around the fracture, so that due to the resultant asymmetry, asymmetries result with regard to the forces introduced into the corticalis of the femur. In patients who, as in this case, have to be supplied with two artificial joints, i.e., with an artificial hip joint and with an artificial knee joint, the question often arises of the mechanical stability of the implant, especially with additional fracture of the femur. This type of difficult indication occurs after severe accidents, for example.

Here again, the endoprosthesis in the invention provides help, since it gives intramedullary support until the ultimate healing of the fracture and can immediately take stress.

The rotational stability of the reinforcing endoprosthesis is advantageously ensured by the fact that the parts that go into the femur have rotationally unsymmetrical contours.

BRIEF DESCRIPTION OF THE DRAWINGS

The present invention will now be described, by way of example only, with reference to the accompanying drawings.

DETAILED DESCRIPTION OF THE INVENTION

Figure 1:
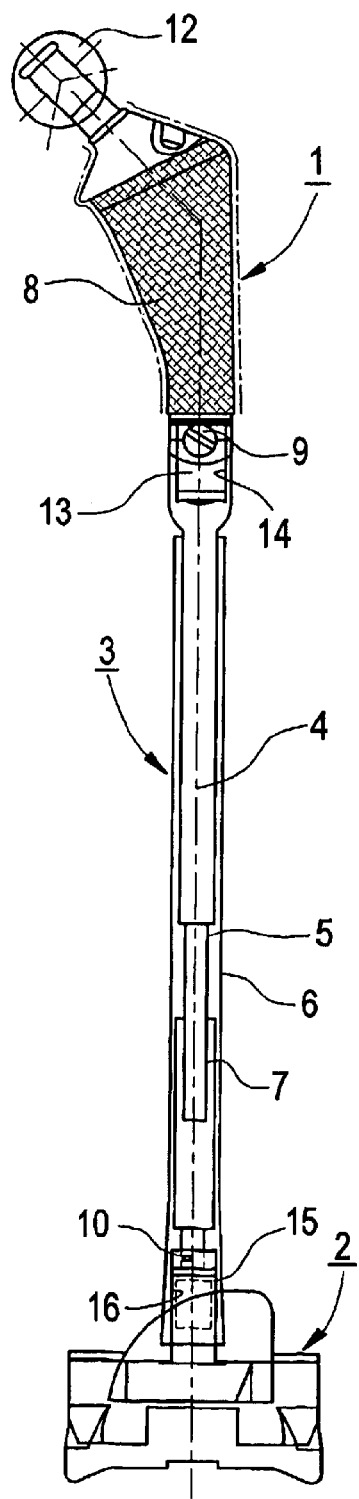
FIG. 1 shows a reinforcing endoprosthesis in one embodiment.

The invention will be explained in greater detail using an example of embodiment.

The shaft part is marked 1, and is set into the resected femoral bone in the hip area. The shaft part 1 holds the artificial ball 12 of the artificial hip joint. The shaft part has a primarily three-dimensional open-mesh spatial network structure 8 in large areas, in which and through which bone material can grow for interior, permanent fixation of the shaft part 1 in the femur.

The intramedullary nail 4 is attached to the distal side of the shaft part 1 by a conical clamping connection between a conical pin 13 molded on the shaft part 1 and a conical clamping receptacle 14, which is provided in an adapter section of the solid intramedullary nail 4. The connection is made with a safety screw 9.

A thread 5 in the form of a threaded spindle is molded on the solid intramedullary nail. The threaded spindle 5 goes into an inner thread 7 in the hollow intramedullary nail 6 in such a way that the length of the connecting part 3 can be adjusted by screw movements of the intramedullary nails 4 and 6.

An adapter section for the condyle part 2 of the artificial knee joint is attached to the second, hollow intramedullary nail 6. To attach the condyle part 2, a conical clamping receptacle 16 is placed in the adapter section, which works with a conical pin 15, which is an integral part of the condyle part 2, in such a way that both parts can be stopped by means of a conical clamping connection.

A hexagon safety screw 10 is provided for rotational safety, only at the transition from the condyle part 2 to the intramedullary nail 6, and it goes into a receptable 11 formed accordingly. This rules out rotation of the condyle part 2 in relation to the rest of the endoprosthesis.

What is claimed is:

1. A reinforcing endoprosthesis for use in a femoral bone resected on both hip and knee ends the endoprosthesis comprising:

a shaft part of an artificial hip joint;

a condyle part of an artificial knee joint; and a connecting part between the shaft part and the condyle part, the connecting part is adapted for use in a femoral bone and includes an intramedullary two-piece nail, wherein one part of the intramedullary nail is a solid intramedullary nail with a threaded projection and a thread on it, and the other part of the intramedullary nail is a hollow intramedullary nail with an inner thread that fits the thread of the first part and can be screwed on with the thread, wherein a length of the endoprosthesis can be adjusted, wherein the connecting part has rotationally unsymmetrical contours.

2. The reinforcing endoprosthesis in claim 1, in which a length of the intramedullary nail can vary by up to 10 cm.

3. The reinforcing endoprosthesis in claim 1, in which a surface of the shaft part and the condyle part is provided, at least in part, with a three-dimensional, open-mesh spatial network structure.

4. The reinforcing endoprosthesis in claim 1, in which the shaft part is stopped on the solid intramedullary nail by means of a safety screw.

* * * * *